(12) United States Patent
Lahaie et al.

(10) Patent No.: US 7,874,470 B2
(45) Date of Patent: Jan. 25, 2011

(54) METHOD AND APPARATUS FOR TESTING SOLDERABILITY OF ELECTRICAL COMPONENTS

(75) Inventors: Denis Lahaie, Guelph (CA); Beverley Howard Christian, Waterloo (CA)

(73) Assignee: Rearch In Motion Limited, Waterloo, Ontario (CA)

( * ) Notice: Subject to any disclaimer, the term of this patent is extended or adjusted under 35 U.S.C. 154(b) by 0 days.

(21) Appl. No.: 12/869,076

(22) Filed: Aug. 26, 2010

(65) Prior Publication Data

US 2010/0320256 A1 Dec. 23, 2010

Related U.S. Application Data

(62) Division of application No. 11/400,233, filed on Apr. 10, 2006.

(51) Int. Cl.
*B23K 31/12* (2006.01)
(52) U.S. Cl. .................................................. 228/103
(58) Field of Classification Search ................. 228/103; 73/866
See application file for complete search history.

(56) References Cited

U.S. PATENT DOCUMENTS

| | | | |
|---|---|---|---|
| 3,627,493 | A | 12/1971 | Manley |
| 5,944,250 | A | 8/1999 | Zagalskiy |
| 6,286,368 | B1 | 9/2001 | Solomon et al. |
| 6,360,935 | B1 | 3/2002 | Flake |
| 6,612,161 | B1 | 9/2003 | Prakash |

(Continued)

FOREIGN PATENT DOCUMENTS

EP 1 236 991 9/2002

(Continued)

OTHER PUBLICATIONS

Co-pending U.S. Appl. No. 11/400,233, "Method and Apparaus for Testing Solderability of Electrical Components", filed Apr. 10, 2006.

(Continued)

*Primary Examiner*—Jessica L Ward
*Assistant Examiner*—Nicholas P D'Aniello
(74) *Attorney, Agent, or Firm*—Bereskin & Parr LLP/S.E.N.C.R.L., s.r.l.

(57) ABSTRACT

The described embodiments relate generally to methods and apparatus for use in determining solderability of an electrical component. One particular aspect relates to apparatus comprising a vacuum chamber, a load sensor, a platform and a control module. The load sensor has a contact portion disposed within the vacuum chamber and the platform is disposed in relation to the contact portion and has a component mounting surface and a mounting member for mounting an electrical component to the component mounting surface. The control module causes relative movement between the platform and the load sensor so that a contact surface of the electrical component is brought into close proximity with the contact portion. When the contact portion has solder thereon and the solder is brought into contact with the contact surface, the load sensor measures force arising from wetting of the solder to the contact surface. The force generated under contact changes over time, depending on the degree of solderability of the electrical component. Thus, measurement of the wetting forces over time provides an indication of the solderability of the electrical component.

20 Claims, 3 Drawing Sheets

U.S. PATENT DOCUMENTS

2002/0027434 A1 3/2002 Nordgren et al.
2002/0157486 A1* 10/2002 Masatoki et al. .............. 73/866
2003/0110844 A1 6/2003 Struckmeier et al.

FOREIGN PATENT DOCUMENTS

JP 05 072153 3/1993
JP 07 072064 3/1995

OTHER PUBLICATIONS

Canadian Office Action dated Nov. 13, 2009, Canadian Patent Application No. 2,583,853.
Humpston et al., "Solder Spread: A Criterion for Evaluation of Soldering", Metallurgical Technology Group GEC Hirst Research Centre Wembly UK, Gold Bulletin Organisation, Jun. 1, 1990, 23 (3), http://www.goldbulletin.org/assets/file/goldbulletin/downloads/Humpston_3_23.pdf.
Robotic Process Systems 6-SIGMA Automatic Wetting Balance Tester, last revised on Dec. 17, 2000, http://web.archive.org/web/20040325135237/www.rpsautomation.com/products/6_sigma.htm.
European Examination Report dated Mar. 24, 2009, European Patent Application No. 08161255.8.
Extended European Search Report dated Nov. 17, 2008, European Application No. 08161255.8.
European Communication Under Rule 71(3) EPC. Application No. 06112413.7. Dated: Mar. 25, 2008.
Solderability Tester—Menisco ST60. Accessed at http://www.metronelec.com/site/home.php?sec=fiche&Idarbo=44&Idarbo1=78&content=1&id=121&lg=2, as early as Jun. 1, 2005.
New solder globule system on solderability tester—Menisco ST60. Accessed at http://www.metronelec.com/site/home.php?sec=fiche&Idarbo=47&content=1&id=125&1g=2, as early as Jun. 1, 2005.
MUST System II Plus Solderability Testing System (product brochure). Accessed at http://www.concoat.co.us/ts_solder.htm, as early as Jun. 1, 2005.
Concoat Solderability Testing. Accessed at http://www.concoat.co.uk/ts_solder.htm, as early as Jun. 1, 2005.
English Abstract of JP 07 072064, published Mar. 17, 1995.
English Abstract of JP 05 072153, published Mar. 23, 1993.
Search and Examination Report for EP 06112413.7, dated Nov. 16, 2008.
Canadian Notice of Allowance. Application No. 2,583,853. Dated: Jul. 21, 2010.

* cited by examiner

METHOD AND APPARATUS FOR TESTING SOLDERABILITY OF ELECTRICAL COMPONENTS

CROSS-REFERENCE TO RELATED APPLICATION

This application is a divisional of application Ser. No. 11/400,233, filed on Apr. 10, 2006, entitled METHOD AND APPARATUS FOR TESTING SOLDERABILITY OF ELECTRICAL COMPONENTS, the entire contents of which are herein incorporated by reference.

TECHNICAL FIELD

The embodiments described herein relate generally to methods and apparatuses for testing the solderability of electrical components, such as surface mount components. In particular, the testing involves automated measurement of surface tension in the solder when contacted with a surface of the component.

BACKGROUND

Many small electronic components are mounted on Printed Circuit Boards (PCB) using surface mount technology (SMT). These SMT components are placed on the appropriate location on the PCB and are subsequently soldered to the PCB by known processes. In order to determine the likelihood of failure of the solder connection between the SMT component and the PCB, it is necessary to perform testing of the solderability of samples of the component.

Current instruments being used for solderability testing essentially include analytical balances with a built-in clock poised over molten solder. The SMT component is suspended from the bottom of the balance prior to testing. The SMT component has flux applied to it and is dipped into the molten solder. The solder may be in a bath or formed as a small globule. The resulting surface tension of the molten solder wetting to the component is measured by the analytical balance over a period of time. The resulting measurements are used to plot a graph of the wetting force (i.e. the surface tension) versus time, which is then used to determine whether the component has suitable wetting properties for providing good solderability. In order for the quality of solderability of the component to be considered adequate, the sample component must wet quickly enough during the time that it is in contact with the molten solder and must exhibit a wetting force large enough to provide a suitably sized solder fillet in the completed solder joint.

Where the testing uses small solder globules, and as available solderability testing instrument pin sizes have decreased from a 4 mm diameter to 1 mm, the limitations of the testing arrangements described above make it difficult to accurately measure the wetting forces of the newest small components. This is in part because of the smaller amounts of solder required for the smaller pins. The sensitivity of the equipment used to measure the wetting forces in such arrangements is inadequate for the smaller wetting forces required to be measured for the smaller SMT pin sizes. Some such arrangements have a smallest full scale division of force measurement in milliNewtons, which is inadequate to measure forces in the order of microNewtons. The newly developed small pin sizes and smaller solder amounts required for such pin sizes means that greater precision in force measurement is needed. However, when measuring such small forces, thermal currents in air at standard pressure may be high enough relative to the small wetting forces that unreliable results would be recorded or the test may be compromised.

Further, arrangements that rely on suspending a sample over molten solder before contacting the solder suffer from non-uniform heating of the component sample. As the heating in a real reflow oven in the normal assembly process is relatively uniform, it is desirable to mimic such conditions during the testing process, if possible. While the above described arrangements can suspend the component sample over the molten solder for a period of time to heat it prior to immersion in the solder, this generally does not result in uniform heating of the component sample.

It is desired to address or ameliorate one or more shortcomings or disadvantages of prior methods and systems for testing the solderability of surface mount components, or to at least provide a useful alternative thereto.

BRIEF DESCRIPTION OF THE DRAWINGS

Embodiments are described in further detail below, by way of example only, with reference to the accompanying drawings, in which.

DETAILED DESCRIPTION

Figure 1:
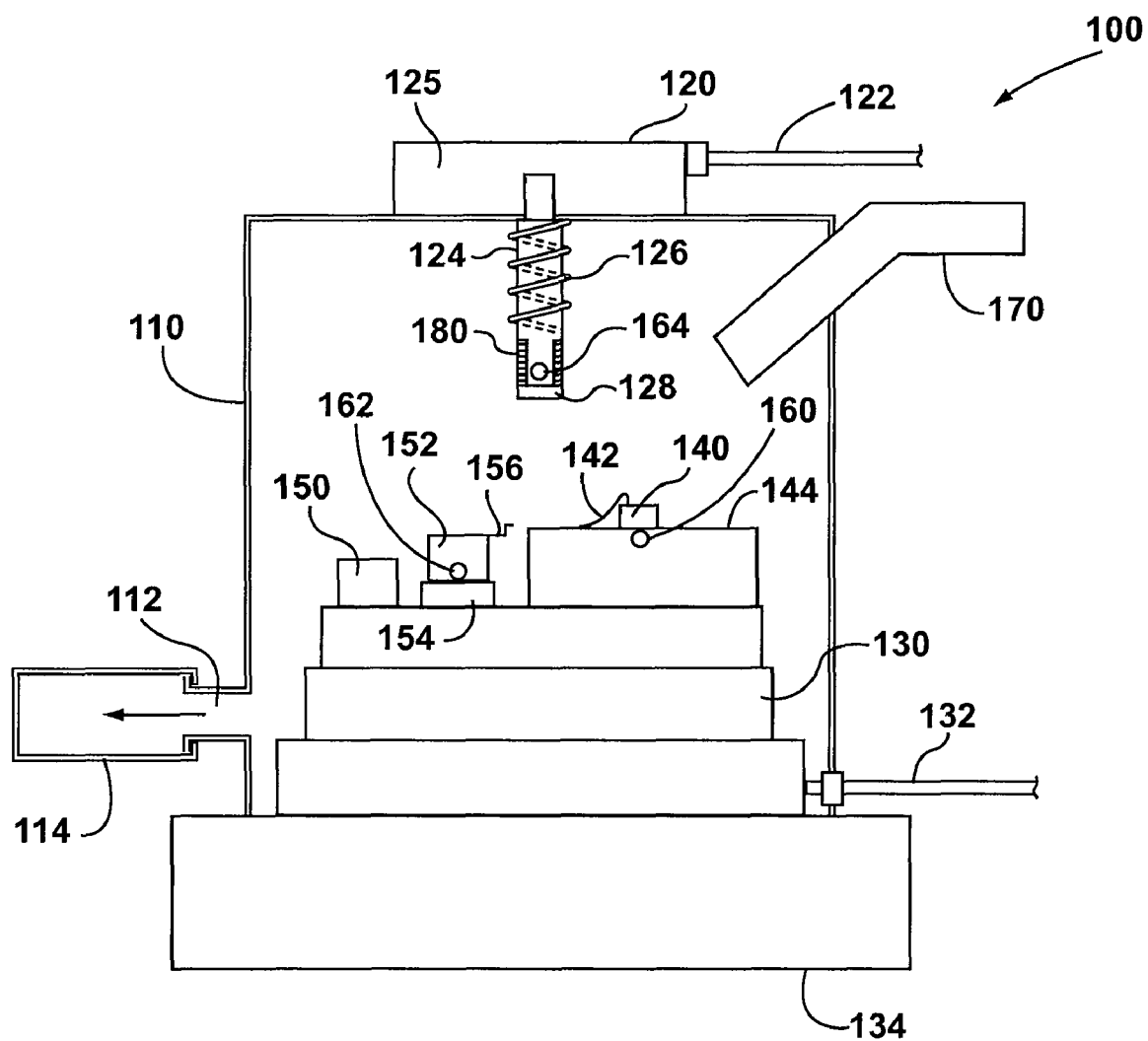
FIG. 1 is a schematic front view of a solderability testing apparatus according to one embodiment.

Embodiments described herein relate generally to methods and apparatus for use in determining solderability of an electrical component. One particular aspect relates to apparatus comprising a vacuum chamber, a load sensor, a platform and a control module. The load sensor has a contact portion disposed within the vacuum chamber. The platform is disposed within the vacuum chamber in relation to the contact portion and has a component mounting surface and a mounting member for mounting an electrical component to the component mounting surface. The control module causes relative movement between the platform and the load sensor so that a contact surface of the electrical component is brought into close proximity with the contact portion. When the contact portion has solder thereon and the solder is brought into contact with the contact surface, the load sensor measures force arising from wetting of the solder to the contact surface. The force occurring under contact changes over time, depending on the degree of solderability of the electrical component. Thus, measurement of the wetting forces over time provides an indication of the solderability of the electrical component.

Providing a vacuum chamber in which the solderability testing can be carried out allows for minimization of thermal currents that might cause spurious results in the surface tension measurements. In one embodiment, a load sensor having a measurement accuracy similar to that of an atomic force microscope may be used. Such precision allows measurement of forces in the order of microNewtons.

In one embodiment, the apparatus comprises a first receptacle containing solder, the first receptacle being positioned on the platform. A first heating element is associated with the first receptacle for heating the solder in the first receptacle. A first temperature sensor is also provided for sensing a temperature of the solder in the first receptacle.

In another embodiment, the apparatus further comprises a second receptacle containing flux, the second receptacle being positioned on the platform. The first and second receptacles have, in one embodiment, closable openings arranged to be closed when the contact portion is not being dipped into the respective first or second receptacle. In another embodiment, a second heating element is disposed on the platform. The second heating element has an upper surface comprising the component mounting surface. The mounting member is disposed on or adjacent the component mounting surface. A second temperature sensor is provided for sensing a temperature of the second heating element.

In one embodiment, the load sensor comprises a projection and the contact portion is disposed at a tip of the projection. The load sensor further comprises a third heating element disposed adjacent the contact portion. A cooling element may also be disposed around the projection distally of the contact portion. The projection comprises a downwardly pending pin of relatively small diameter, for example in the order of 0.5 mm or less. The platform is disposed below the contact portion of the projection. The contact portion is formed of a material that is electrically and thermally minimally—or non-conductive.

Another particular aspect relates to a method for measuring solderability of an electrical component. The method comprises the steps of: mounting at least one electrical component to a component mounting surface within a vacuum chamber; applying flux to a contact portion of a load sensor, the contact portion being disposed within the vacuum chamber; creating a vacuum in the vacuum chamber; applying solder to the contact portion; causing relative movement between the at least one electrical component and the contact portion so that a respective electrical component is brought into close proximity with the contact portion and the solder contacts a contact surface of the electrical component; and measuring by the load sensor force arising from wetting of the solder during contact with the contact surface.

The method may be used to measure the solderability of more than one electrical component and/or more than one surface of a component, in which case the steps of applying flux, applying solder, causing relative movement and measuring the surface tension are repeated for each electrical component and/or surface.

The at least one electrical component is disposed below the contact portion. Further, the step of causing relative movement comprises moving the at least one electrical component relative to the contact surface while the contact surface is held stationary. The step of applying flux comprises moving a flux container containing flux relative to the contact portion to dip the contact portion into the flux container. The step of applying solder comprises moving a solder container containing solder relative to the contact portion to dip the contact portion into the solder container. In order to achieve the relative movement of the electrical component, the flux container and the solder container, each is mounted to a moveable platform within the vacuum chamber or a member supported by the platform.

Another particular aspect relates to a system for measuring solderability of an electrical component. The system comprises a vacuum chamber, a load sensor, a support, a control module, a computer processor and a memory. The load sensor has a contact portion which is disposed within the vacuum chamber. The support is disposed within the vacuum chamber in relation to the contact portion and has a component mounting surface for mounting the electrical component. The control module is configured to cause relative movement between the support and the load sensor so that a contact surface of the electrical component is brought into close proximity with the contact portion. When the contact portion has solder thereon and the solder is brought into contact with the contact surface, the load sensor measures force arising from wetting of the solder to the contact surface. The memory stores computer program instructions which, when executed by the computer processor, cause the computer processor to control operation of the load sensor and the control module.

Yet another aspect relates to computer readable storage storing computer program instructions which, when executed by a computer system, cause the computer system to control an apparatus comprising a vacuum chamber and a load sensor, the load sensor having a contact portion disposed within the vacuum chamber. Execution of the stored computer program instructions by the computer system causes the computer system to control the apparatus to: apply flux to the contact portion; create a vacuum in the vacuum chamber; apply solder to the contact portion; cause relative movement between an electrical component and the contact portion so that the electrical component is brought into close proximity with the contact portion and the solder contacts a contact surface of the electrical component; and measure by the load sensor force arising from wetting of the solder during contact with the contact surface.

Referring now to FIG. 1, there is shown a schematic front view of an example testing apparatus 100 for testing the solderability of electrical components 140, such as SMT components, by measuring wetting forces (i.e. surface tension) during contact of solder to the electrical components 140. The schematic of the apparatus shown in FIG. 1 is not to scale and is provided for purposes of illustration only.

The testing apparatus 100 has a vacuum chamber 110 with a load sensor 120 mounted thereon and a support module platform 130 contained within the vacuum chamber 110. One or more electrical components 140 are mounted to, or otherwise held on, a heating element 144 that is situated on the platform 130. Also situated on platform 130 are a flux receptacle, such as flux container 150, and a solder receptacle, such as solder container 152. The vacuum chamber 110 also has an imaging device 170, such as a camera, directed to capture images during testing. The images can be viewed by the test supervisor to make positioning adjustments during testing, if necessary.

Vacuum chamber 110 is preferably formed as a cabinet and has an opening (not shown), such as a door, for receiving the electrical components and consumable materials, such as flux and solder. This opening must be closable and sealable so as to be air tight, but otherwise may take any suitable shape or form. Vacuum chamber 110 is supported by a vibration table 134 that is suitable for maintaining the vacuum chamber 110 motionless despite external vibrations or movements that would otherwise be transmitted through the structure supporting the vacuum chamber 110. Thus, the vibration table 134 prevents transmission of any such external vibrations or movements to the platform 130 and other parts in the vacuum chamber 110, thereby providing greater reliability of test results. The vibration table 134 may include a pneumatic vibration isolation system such as is commercially available.

Vacuum chamber 110 also comprises an outlet 112 through which air and other gases are withdrawn from the vacuum chamber 110 (when sealed). A vacuum pump 114 or other vacuum generating device is used to depressurize the internal volume of vacuum chamber 110 and thus create a vacuum therein. Vacuum chamber 110 is suitably sealed against inadvertent depressurization. Vacuum pump 114 may be a suitable commercially available roughing pump or roughing/diffusion pump system, for example. Vacuum pump 114 preferably has a pressure sensor associated therewith and a suitable input/output interface for external computer control of the vacuum pump 114. Alternatively, the vacuum pump may not interface with an external control device and may be manually operated by the test supervisor.

Moveable support platform 130 is positioned within vacuum chamber 110 and is movable inside the vacuum chamber 110 in three dimensions, along X, Y and Z axes. The movement of platform 130 is bounded by the confines of vacuum chamber 110 and is controlled by servo motors (not shown) in platform 130 that are driven by control signals received via control cable 132. Platform 130 may be any suitable commercially available XYZ stage with high resolution positioning in at least the vertical axis. Such resolution is at least of micrometer precision.

Flux container 150 may be supported directly by platform 130 or by a support member interposed between the flux container 150 and platform 130. Flux container 150 is preferably formed of steel and has a closeable opening at the top for allowing tip portion 128 of load sensor 120 to be dipped into flux contained in flux container 150. The closeable opening of the flux container 150 is preferably biased towards a closed position, for example by spring loading. Preferably, the closable opening is automatically opened by some form of mechanical actuation when tip portion 128 is positioned above flux container 150 and is brought within a predetermined vertical distance of the opening.

Solder container 152 is preferably positioned on a heating plate 154, which is situated on platform 130. Heating plate 154 preferably has a resistive heating element therein and is thermally insulated from platform 130. Alternatively, instead of heating element 154 being formed as a plate, it may be formed as a coil around the outside of solder container 152 or it may use an alternative heat source.

In order to sense the temperature of the solder in solder container 152, a temperature sensor 162, as such as a thermocouple, is positioned to take temperature measurements corresponding to the temperature of the solder in solder container 152. Instead of a thermocouple, the temperature can be measured using a thermal camera. Like flux container 150, solder container 152 has a closeable opening at its top which is biased towards a closed position but which is openable for dipping tip portion 128 into the solder. The closeable opening of solder container 152 is preferably opened automatically by a form of mechanical actuation when tip portion 128 is positioned above solder container 152 and approaches within a predetermined vertical distance of the opening. Solder container 152 preferably also has an automatic or mechanically actuable wiper 156 for removing dross from the top of the molten solder. The solder container 152 is preferably formed of tungsten. The heating plate may be formed of a suitable material for resistance heating, such as an iron-nickel-chromium alloy, a nickel-chromium alloy, Inconel™ or Kanthal™.

Heating element 144 may be of any suitable commercially available type having a relatively small surface area (but relatively large compared to the electronic components) and with good spatial temperature control so as to provide even heating across the surface that supports the electrical components. Heating element 144 may have a temperature sensing device 160, such as a thermocouple, integrally formed therein or separately formed but appropriately positioned so as to sense a temperature of the upper surface of heating element 144 to which the electrical components 140 are secured or mounted. Temperature sensing device 160 may alternatively employ a thermal imaging camera.

Each electrical component 140 is secured to the top surface of heating element 144. This surface may be used as the mounting surface for mounting only a single electronic component 140 or it may be used to mount a number of electronic components 140 in series, for example in the order of ten or so. Each electronic component 140 is secured to the mounting surface of heating element 144 by a mounting member 142, which may be in the form of a clip, arm, bracket or other mechanical means for securing the electrical component 140 against inadvertent movement on the mounting surface during the testing. Alternatively, other means may be used to secure the electrical components 140 to the mounting surface, such as suction, adhesion or magnetic attraction.

Load sensor 120 is of a suitable commercially available type having microNewton measurement accuracy, such as an atomic force microscope (AFM), for example. Load sensor 120 is positioned on top of the vacuum chamber 110 so as to reside partly outside of the vacuum chamber 110 and partially within the vacuum chamber 110. Load sensor 120 has a downwardly projecting pin 124 that is disposed mostly within the vacuum chamber 110 but is connected to a measurement and control portion 125 that is positioned outside of the vacuum chamber 110. Pin 124 is used to measure the wetting forces during testing. The forces exerted on pin 124 are sensed by known elements within the measurement and control portion 125. Load sensor 120 communicates with an external computer system 210 (shown in FIG. 2 and described in further detail below) via a suitable communications cable 122. In an alternative embodiment, load sensor 120 may be located entirely with vacuum chamber 110.

Pin 124 is preferably formed of a material that is non-conductive electrically and thermally. Pin 124 is preferably formed of alumina. Alternatively, pin 124 may be formed of a silicon carbide, silicon nitride or zirconia. Pin 124 may be approximately cylindrical or may have an alternative elongate shape with a small thickness or diameter. The diameter of pin 124 may be about 0.5 mm, for example.

Pin 124 may have a cooling coil 126 disposed along a portion of pin 124 proximally of contact tip portion 128. Pin 124 preferably also has a third heating element 180 for resistive heating of tip portion 128. Because tip portion 128 needs to be heated to a relatively high temperature by heating element 180, cooling element 126 is used to reduce heat conduction to the measurement and control portion 125 of load sensor 120.

Tip portion 128 is preferably formed of iron. The heating element 180 may be formed of an iron nickel chromium alloy. Alternatively the resistance heating element 180 may be formed of a nickel chromium alloy, Inconel™ or Kanthal™. The downwardly facing surface of tip portion 128 is that which is fluxed and dipped in solder container 152 and is of a sufficient dimension to retain a small but appropriately sized and cohesive globule of solder thereon through surface tension, despite the pull of gravity.

A temperature sensor 164 is positioned toward the end of pin 124, adjacent to portion 128 and distal (i.e. toward the tip) of cooling element 126. Temperature sensor 164 is positioned to sense the temperature of tip portion 128. For this purpose, a thermocouple may be used or, alternatively, a thermal imaging camera may be used. The temperature sensors 160, 162 and 164 shown in FIG. 1 are thermocouples and are preferably of type T or K with a linear response in the 0 to 300° Celsius range. If thermal imaging cameras are used, these will not be positioned as indicated by the reference indicators in FIG. 1 or temperature sensors 160, 162 and 164, but will instead be positioned away from, but directed toward, the location at which it is desired to sense the temperature. Such thermal imaging cameras may be mounted on an interior wall of the vacuum chamber, for example, and trained on their respective points of interest.

Figure 2:
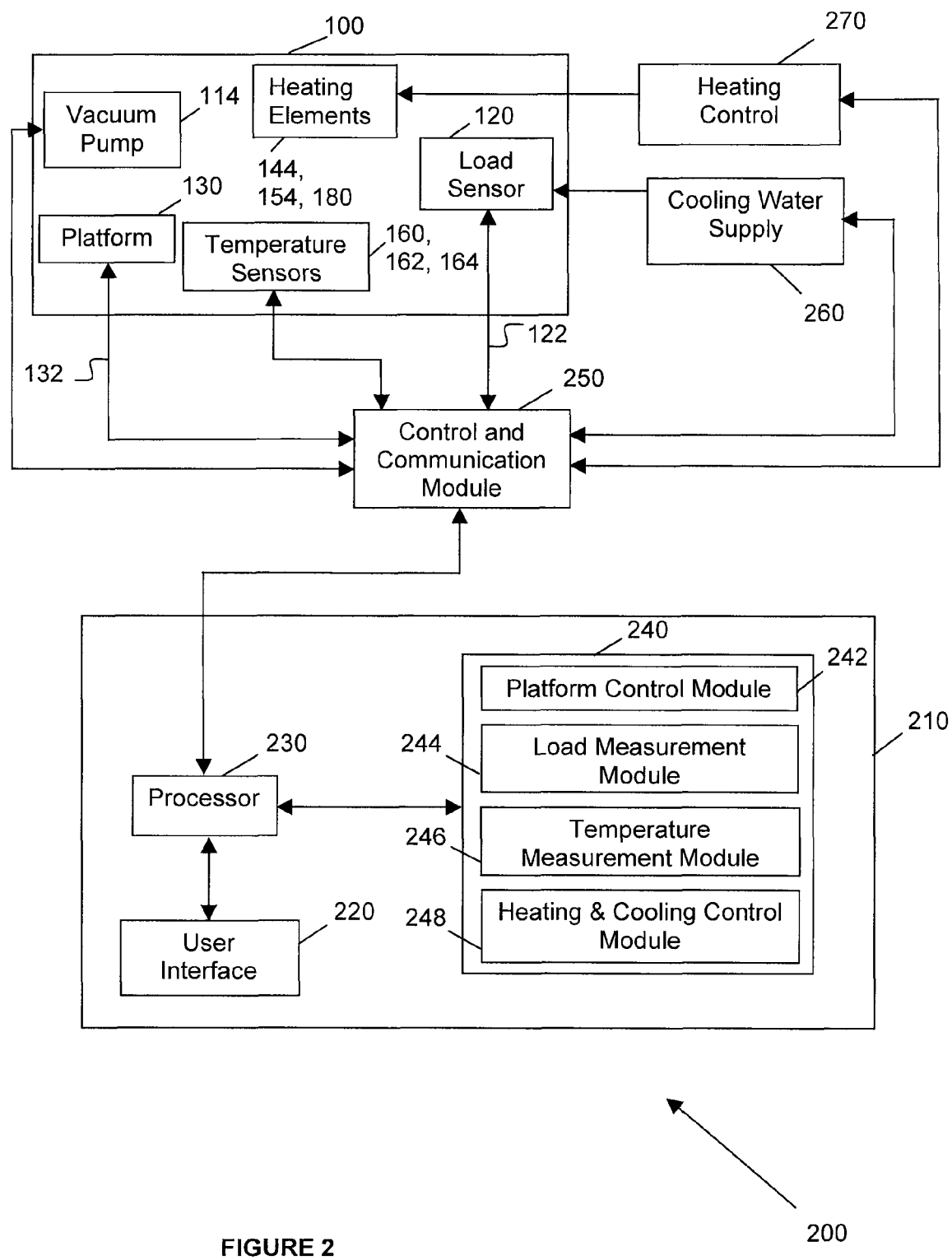
FIG. 2 is a block diagram of a system for testing solderability, including the apparatus of FIG. 1.

Referring also to FIG. 2, there is shown a system 200 for testing the solderability of electrical components 140. System 200 includes the apparatus 100 and a computer system 210 for controlling the apparatus 100 to perform the solderability testing. System 200 further comprises a control and communication module 250 for enabling computer system 210 to provide control signals to components within apparatus 100 and to receive output signals from those components where appropriate. Control and communication module 250 also performs analog-to-digital and digital-to-analog conversion functions, where appropriate. System 200 further comprises a cooling water supply 260 and a heating control module or circuit 270. Cooling water supply 260 provides cooling water to cooling element 126 in load sensor 120 and heating control module 270 controls power to heating elements 144, 154 and 180.

Computer system 210 comprises a user interface 220 to allow a supervisor of the solderability testing to configure and initiate the testing procedure. Computer system 210 also comprises a processor 230 in communication with the user interface 220 and a memory 240 accessible to processor 230. Memory 240 stores computer program instructions which make up software modules used by system 200 during the solderability testing procedure. Such software modules include, for example, a platform control module 242, a load measurement module 244, a temperature measurement module 246 and a heating and cooling control module 248. Processor 230 accesses the computer program instructions of each of the software modules in memory 240 and executes the instructions as appropriate, including, for example, transmitting control instructions to control and communication module 250 to operate the various elements within apparatus 100.

Sensed conditions within apparatus 100, for example such as the internal pressure of the vacuum chamber 110, the platform position, the sensed temperatures, and optionally the images being received at camera 170, are monitored by processor 230 via control and communication module 250. Such sensed conditions are used by the software modules to ensure that the testing procedure is being carried out according to preconfigured testing parameters. The output of camera 170 may be provided directly to a display independent of computer system 210 or it may be provided to a suitable image processor within computer system 210 for display via user interface 220.

User interface 220 may include any suitable interface means, such as a display, keyboard and mouse. One or more of the software modules stored in memory 240 may include existing software applications, for example such as those which may be provided with the purchase of elements in apparatus 100. For example, load sensor 120 may have appropriate software that is commercially available with purchase of load sensor 120 and which may constitute the load measurement module 244. Additionally, platform control module 242 may comprise software provided by the maker of platform 130 and specifically tailored for control of platform 130. Other of the software modules stored in memory 240 may include routines developed in an appropriate commercially available software application for control and measurement purposes, such as LabVIEW™ available from National Instruments.

Figure 3:
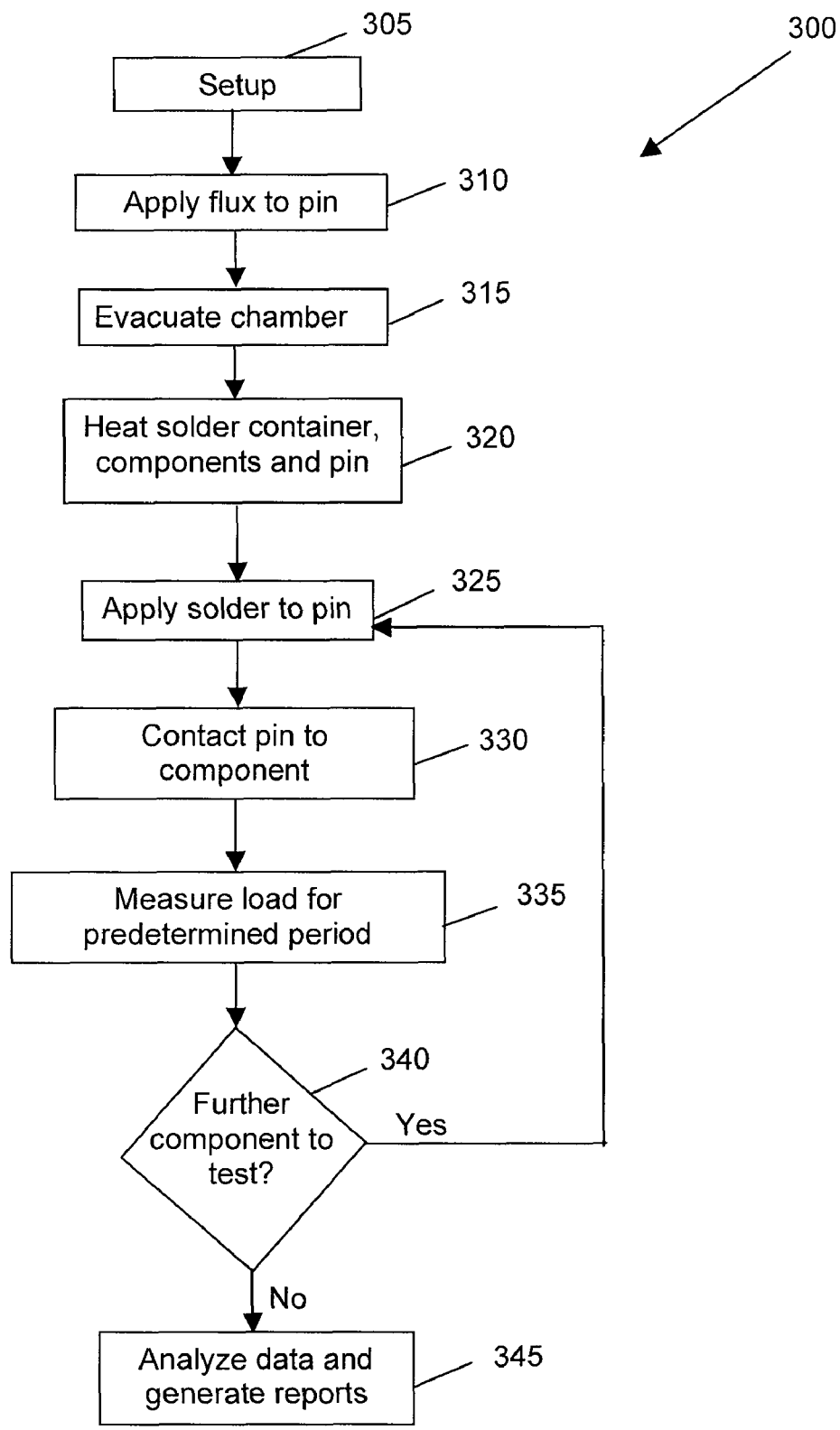
FIG. 3 is a flow diagram of a method of measuring the solderability of electrical components.

Referring now to FIG. 3, a method 300 of testing the solderability of electrical components is described in further detail. Method 300 begins at step 305 with a set up procedure. In the set up procedure, the vacuum chamber 110 is not sealed and its opening may be open. During the set up procedure, the flux container 150 is filled with flux if required and the solder container 152 is filled with a suitable volume of solid solder, if required. One or more electrical components 140 are positioned on the mounting surface of heating element 144 and the electrical components 140 are fixed in place using the mounting members 142 or alternative means of securement. When the electrical components 140 are secured on the mounting surface, they are placed so as to have their test surfaces in a horizontal position and face up. The mounting members 142 should be positioned so as not to obstruct contact between the testing surfaces of the electrical components 140 and the contact tip portion 128 during testing.

Set up step 305 may also include verifying the operational status of each of the components of apparatus 100. For example, the operability of vacuum pump 114 may be checked, along with the operational status of the other sensing and control elements in apparatus 100, such as platform 130, camera 170, load sensor 120, the heating elements 144, 154 and 180 and the temperature sensors 160, 162 and 164.

Once the set up procedure is complete, the opening of vacuum chamber 110 is closed and flux is applied to pin 124, at step 310. In order to apply flux to pin 124, platform 130 is moved according to control signals received through cable 132 so as to position flux container 150 beneath tip portion 128 and platform 130 is then slowly raised so as to dip tip portion 128 into flux container 150 and immerse it in flux. Tip portion 128 is then withdrawn from flux container 150 by lowering platform 130 and the opening of flux container 150 is closed in order to prevent evaporation of the flux. Preferably, about 2.5 mm of the pin 124 is lowered into the flux container 150.

At step 315, vacuum chamber 110 is sealed and evacuated through outlet 112 by vacuum pump 114. Vacuum pump 114 depressurizes the vacuum chamber 110 so as to reduce the pressure within vacuum chamber 110 to a predetermined pressure level of about 0.01 torr, for example. The pressure inside vacuum chamber 110 should be low enough that thermal conduction currents are negligible, but the higher the pressure that can be tolerated, the better. The higher the pressure that can be tolerated, the fewer practical difficulties are encountered with maintaining the vacuum conditions.

At step 320, following evacuation of vacuum chamber 110, solder container 152 is heated by heating element 154 to ensure that the solder therein is in a molten state. If necessary, wiper 156 is used to wipe the dross from the top of the molten solder once it has melted. While the solder is melted, heating elements 144 and 180 are used to heat the electrical components 140 and tip portion 128, respectively.

Once the solder, the electrical components 140 and the tip portion 128 are all heated to the desired degree, as sensed by respective temperature sensors 162, 160 and 164, solder is applied to tip portion 128 of pin 124. The electrical components 140 should be heated to about 100 degrees Celsius, while the solder and tip portion 128 should be heated to temperatures above the melting point of the solder, which may vary according to the type of solder.

Application of solder to tip portion 128 is done by moving platform 130 so as to position solder container 152 beneath tip portion 128 and then raising platform 130 so as to immerse tip portion 128 in solder container 152 by about 2.5 mm. During or prior to solder container 152 being raised towards tip portion 128, its top opening is opened and, once tip portion 128 is withdrawn, the opening is again closed. Once solder has been applied to the tip portion 128 and platform 130 has been lowered to withdraw tip portion 128 from solder container 152, camera 170 may be used to visually verify that an appropriate amount of solder is suspended from tip portion 128. Signals from load sensor 120 may also be used to verify that an appropriate amount of solder is suspended from tip portion 128.

At step 330, platform 130 is again moved relative to pin 124 so as to bring a testing surface of electrical component 140 into contact with the globule of solder suspended from tip portion 128. This contact is achieved slowly and with great precision. Once load sensor 120 detects the exertion of a wetting force brought about by contact of the solder on tip portion 128 with a test surface of electrical component 140, a signal is sent by load sensor 120 to processor 230 via cable 122 and processor 230 then instructs platform 130 (via cable 132) to cease movement. The load sensor may wait until it detects force above a predetermined threshold before causing the platform 130 to stop.

Once platform 130 has stopped moving electrical component 140 towards tip portion 128, load sensor 120 measures the forces exerted on pin 124 by surface tension resulting from the wetting of the solder to the test surface of electrical component 140. The wetting forces are measured for a predetermined period of time, for example such as 5 to 20 seconds or until the forces reach an equilibrium, depending on the sample being tested, and the measurements are uploaded from load sensor 120 to processor 230 in real time and recorded by processor 230 in memory 240. Contact of the solder on pin 124 with the electrical component should be made in such a way as to avoid the solder sliding off tip portion 128. Otherwise, the value of the test data will be minimal.

At step 340, processor 230 may determine that, according to the preconfigured testing procedure, there are further electrical components 140 on the mounting surface that remain to be tested or the same electrical component 140 has a further surface to be tested. Alternatively, this determination may be made by the test supervisor. Either way, steps 325 to 335 are repeated for each such further electrical component 140 or surface. Once testing has been performed on all electrical components 140 on the mounting surface and all component surfaces, processor 230 analyzes the measured test data and generates one or more reports, at step 345, for presentation to the test supervisor. Such reports may include, for example, plots of the buoyancy and wetting forces as a function of time and a summary of the test conditions.

While method 300 is preferably performed in the order of the steps described above, alternative embodiments may reverse the order of some of the steps. For example, the order of steps 315 and 320 may be reversed.

It should be understood that a reference herein to a test surface of an electrical component includes conductive pads and other forms of electrical terminations or leads. Further, while reference is made herein to SMT components as one form of electrical component, it should be understood that other kinds of electrical components that rely on solder to form electrical connections on current boards may be the subject of testing using the described embodiments.

The invention claimed is:

1. A method for use in determining solderability of an electrical component, the method comprising the following acts in the order presented:

mounting at least one electrical component to a component mounting surface within a vacuum chamber;

applying flux to a contact portion of a load sensor, the contact portion being disposed within the vacuum chamber;

creating a vacuum in the vacuum chamber;

applying solder to the contact portion;

causing relative movement between the at least one electrical component and the contact portion so that a respective electrical component is brought into close proximity with the contact portion and the solder contacts a contact surface of the respective electrical component; and measuring by the load sensor force arising from wetting of the solder during contact with the contact surface.

2. The method of claim 1, wherein the at least one electrical component comprises at least two electrical components and the method further comprises, for each electrical component, the applying flux to the contact portion, the applying solder to the contact portion, the causing relative movement and the measuring by the load sensor.

3. The method of claim 1, wherein the at least one electrical component is disposed below the contact portion and wherein the causing relative movement further comprises moving the at least one electrical component relative to the contact surface while the contact surface is held stationary.

4. The method of claim 1, wherein the applying flux to the contact portion further comprises moving a flux container containing flux relative to the contact portion to dip the contact portion into the flux container.

5. The method of claim 4, wherein the contact portion of the load sensor is dipped into the flux container to a depth of about 2.5 mm.

6. The method of claim 1, wherein the applying solder to the contact portion further comprises moving a solder container containing solder relative to the contact portion to dip the contact portion into the solder container.

7. The method of claim 6, wherein the applying solder to the contact portion further comprises heating the solder container to turn the solder contained therein in a molten state.

8. The method of claim 6, wherein the applying solder to the contact portion further comprises heating the electrical component.

9. The method of claim 6, wherein the applying solder to the contact portion further comprises heating the contact portion of the load sensor to a temperature above the melting point of the solder.

10. The method of claim 6, wherein the contact portion of the load sensor is dipped into the solder container to a depth of about 2.5 mm.

11. The method of claim 1, wherein the creating a vacuum further comprises reducing the pressure in the vacuum chamber to about 0.01 torr.

12. The method of claim 1, wherein each at least one electrical component has a plurality of contact surfaces and the method further comprises, for each contact surface, the applying flux to the contact portion, the applying solder to the contact portion, the causing relative movement and the measuring by the load sensor.

13. The method of claim 1, wherein the mounting at least one electrical component further comprises fixing the at least one electrical component to the component mounting surface using a mounting member.

14. The method of claim 1, wherein the at least one electrical component are mounted to the component mounting surface so that the contact surface is upwardly facing.

15. The method of claim 14, wherein the contact portion of the load sensor is downwardly facing.

16. The method of claim 1, further comprising ceasing relative movement between the at least one electrical component and the contact portion when the load sensor measures the force arising from wetting of the solder.

17. The method of claim 16, further comprising ceasing the relative movement between the at least one electrical component and the contact portion when the load sensor measures force above a predetermined threshold.

18. The method of claim 1, wherein the measuring by the load sensor further comprises measuring the force arising from wetting of the solder for a predetermined period of time.

19. The method of claim 18, wherein the predetermined period of time is between 5 and 20 seconds.

20. The method of claim 1, wherein the measuring by the load sensor further comprises measuring the force arising from wetting of the solder until the force reaches equilibrium.

* * * * *